US00PP13397P3

(12) United States Plant Patent
Noodelijk

(10) Patent No.: US PP13,397 P3
(45) Date of Patent: Dec. 24, 2002

(54) CHRYSANTHEMUM NAMED 'MINERVARES'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/734,604

(22) Filed: Dec. 13, 2000

(65) Prior Publication Data

US 2002/0092061 P1 Jul. 11, 2002

(51) Int. Cl.[7] ..... A01H 5/00
(52) U.S. Cl. ..... Plt./287
(58) Field of Search ..... Plt./287, 289

(56) References Cited

PUBLICATIONS

UPOV–Rom hit on 'Minerva', Plant Variety Database, GTI-Jouve Retrieval Software, 2001/04.*

* cited by examiner

*Primary Examiner*—Bruce R. Campell
*Assistant Examiner*—Anne Marie Grünberg
(74) *Attorney, Agent, or Firm*—Parkhurst & Wendel, L.L.P

(57) ABSTRACT

A chrysanthemum plant named 'Minervares' characterized by its medium sized blooms with white ray florets and prolific branching; natural season flower date September 1–6; blooming for a period of 5 weeks.

3 Drawing Sheets

BACKGROUND OF THE INVENTION

'Minervares' is a product of a breeding and selection program for outdoor pot mums (garden mums) which had the objective of creating new chrysanthemum cultivars with a decorative type flower, a natural season flower date around September 1–6; blooming for a period of 5 weeks. The new plant of the present invention comprises a new and distinct cultivar of Chrysanthemum plant 'Minervares' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout, Holland in September 1998. The plant has been asexually reproduced by cuttings in greenhouses at Rijsenhout, Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
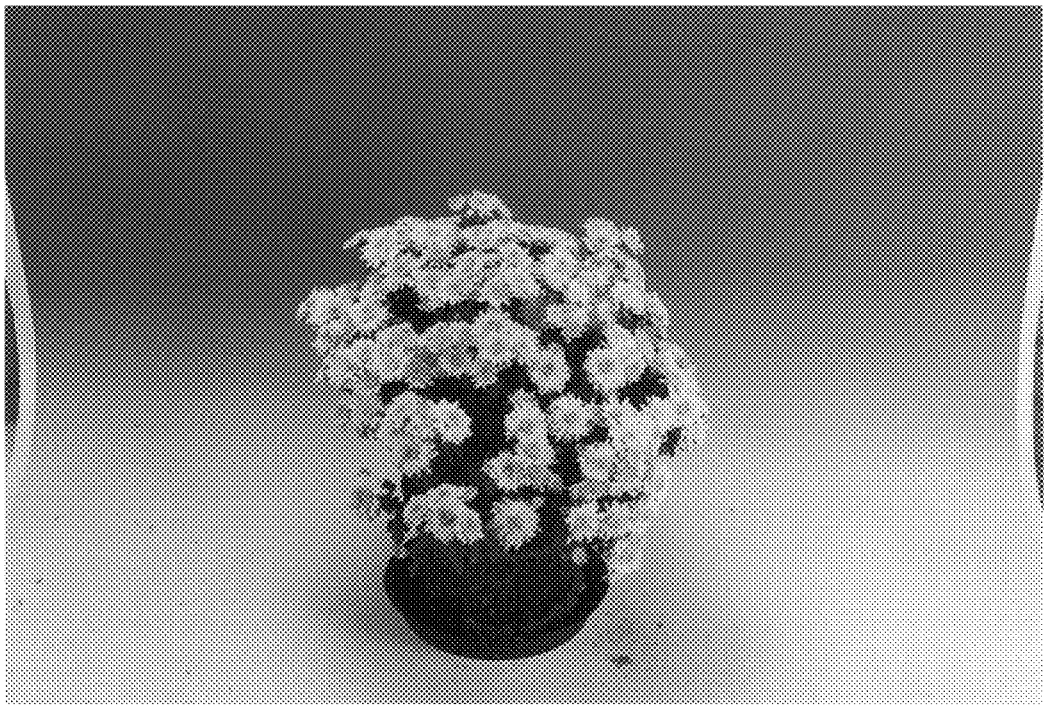
FIG. 1 shows a plant of the cultivar in full bloom.
Figure 2:
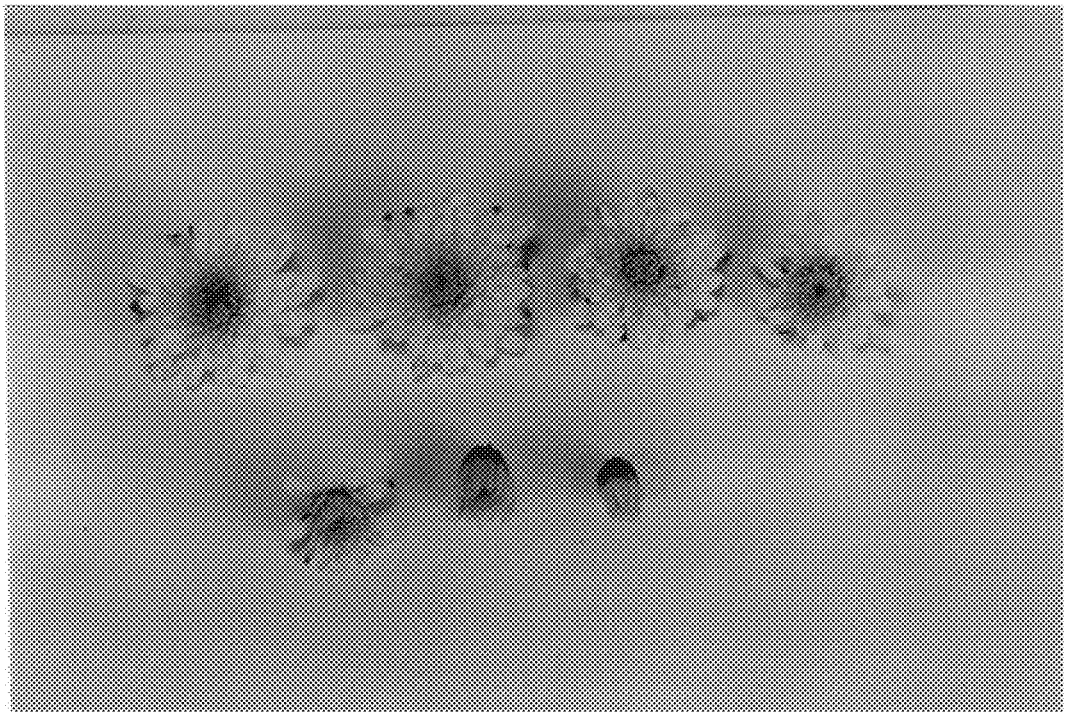
FIG. 2 shows the various stages of bloom of the new cultivar.
Figure 3:
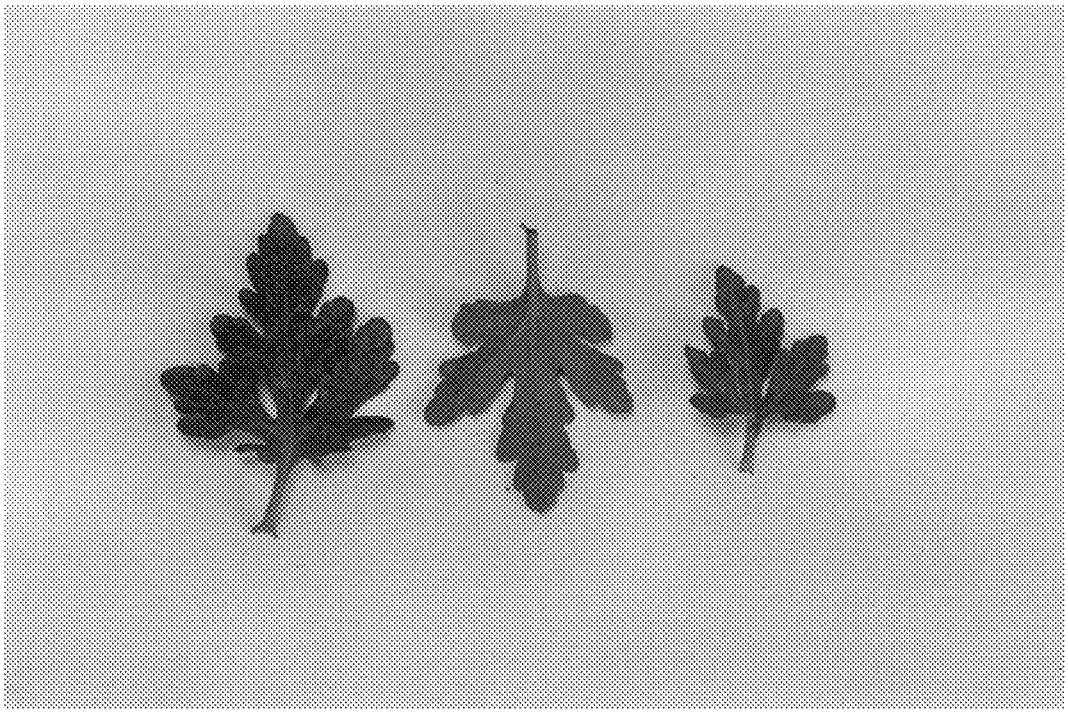
FIG. 3 shows the various stages of foliage and petiole of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 1999 and 2000. The natural blooming date of this crop was September 1–6 (week 36). The average height of the plants was 35–40 cms. No growth retardants were used. No tests were done on disease or insects resistance or susceptibility. No tests were done on cold or drought resistance. This new variety produces medium sized blooms with white ray florets and a yellow disc-florets blooming for a period of 5 weeks.

From the cultivars known to inventor the most similar existing cultivar in comparison to 'Minervares' is 'TOLIMA' (U.S. Plant Pat. No. 6,988). When 'TOLIMA' and 'Minervares' are being compared the following differences are noticed: The differences of 'TOLIMA' and 'Minervares' are (1) Flower form. The flowers of 'TOLIMA' are more decorative (2) Flower color. The flowers of 'TOLIMA' are more pure white (less cream white) (3) Natural blooming date. 'Minervares' flowers earlier.

The following is a description of the plant and characteristics that distinguish 'Minervares' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1: Botanical Description of CULTIVAR 'Minervares'

Bud:
- *Size.*—Small; cross-section 1.0 cm, height 0.7 cm.
- *Outside color.*—Green-yellow 1 D.
- *Involucral bracts.*—2 rows, length 7 mm, width 3 mm.
- *Involucral bracts among disc-florets.*—Not present.
- *Involucral bracts color.*—Green 138 B.

Bloom:
- *Type.*—Duplex daisy.
- *Height.*—Flat, 1.2–1.5 cm.
- *Size.*—Medium.

*Fully expanded.*—4.5–5.0 cm.
*Number of blooms per branch.*—Approx. 4–5 blooms per branch.
*Performance on the plant.*—5 weeks.
*Seeds* (*if crossed*).—Produced in large quantities, ovate. Grey-brown 199 A, 2 mm in length.
*Fragrance.*—Typical chrysanthemum.

Color:
*Center of the flower* (*disc-florets*).—Immature green-yellow 1 D. Mature yellow 12 A.
*Color of upper surface of the ray-florets.*—Yellow 4 D.
*Color of the lower surface of the ray-florets.*—White 155 B.
*Tonality from distance.*—A garden mum with white flowers and a yellow disc.
*Color of the upper surface of the flowers after aging of the plant.*—White 155 B.

Ray florets:
*Texture.*—Upper and under side smooth.
*Number.*—80–100.
*Cross-section.*—Flat.
*Longitudinal axis of majority.*—Straight, sometimes reflexing.
*Length of corolla tube.*—Short, 0.5–0.7 cm.
*Ray-floret margin.*—Entire.
*Ray-floret length.*—2.2–2.5 cm.
*Ray-floret width.*—0.4–0.7 cm.
*Ratio length/width.*—Medium.
*Shape of tip.*—Dentate.

Disc florets:
*Disc diameter.*—0.7 cm.
*Distribution of disc florets.*—Numerous, visible at a mature state of flowering.
*Shape.*—Tubular.
*Color.*—Yellow 12 A.
*Receptacle shape.*—Conical raised.

Reproductive organs:
*Stamen* (*present in disc florets only*).—Thin, 3 mm in length.
*Stamen color.*—Yellow-green 144A.
*Pollen.*—Present.
*Pollen color.*—Yellow 12 A.
*Styles.*—Thin.
*Style color.*—Yellow-green 144 A.
*Style length.*—4 mm.
*Stigmas color.*—Yellow-green 144 A.
*Stigma width.*—1 mm.
*Ovaries.*—Enclosed in calyx.

Plant:
*Shape.*—Semi upright.
*Growth habit.*—Spreading.
*Growth rate.*—Rapid.
*Height.*—35–40 cm.
*Width.*—30–35 cm.
*Stem color.*—Green 138 B.
*Stem strength.*—Strong.
*Stem brittleness.*—Present.
*Stem anthocyanin coloration.*—Absent.
*Length of lateral branch.*—From top to bottom 15–17 cm.
*Lateral branch color.*—Green 138 B.
*Lateral branch, attachment.*—Strong.
*Branching* (*average number of lateral branches*).—Prolific with 6–7 breaks after pinching.
*Peduncle length.*—4.0–4.5 cm.
*Peduncle color.*—Green 138 B.
*Natural season blooming date.*—September 1–6.

Foliage:
*Color of mature leaves.*—Upper side yellow-green 147 B. Under side yellow-green 147 C.
*Color of immature leaves.*—Upper side yellow-green 146 A. Under side yellow-green 146 B.
*Size.*—Small; length 4.5 cm, width 4.0 cm.
*Quantity* (*number per lateral branch*).—13–15.
*Shape.*—Round.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Acute.
*Margin of sinus between lateral lobes.*—Converging.
*Shape of base.*—Truncate.
*Apex.*—Mucronate.

TABLE 2

Differences with the comparison varieties (when grown under the same conditions)

| | 'Minervares' | 'TOLIMA' |
|---|---|---|
| Flower form | Duplex daisy | Decorative |
| Flower color | Creamy white, with a yellow white center | More pure white, center is slightly cream white |
| Natural blooming date | September 1–6 | September 22–26 |

I claim:

1. A new and distinct variety of chrysanthemum plant as described and illustrated.

* * * * *